US00PP21305P2

(12) United States Plant Patent
Parham

(10) Patent No.: US PP21,305 P2
(45) Date of Patent: Sep. 21, 2010

(54) ***CHRYSANTHEMUM* PLANT NAMED 'LETITIA TIME SUNNY'**

(50) Latin Name: *Chrysanthemum morifolium*
Varietal Denomination: Letitia Time Sunny

(75) Inventor: Ruth Parham, Bognor Regis (GB)

(73) Assignee: Cleangro Ltd, Chichester, West Sussex (GB)

( * ) Notice: Subject to any disclaimer, the term of this patent is extended or adjusted under 35 U.S.C. 154(b) by 0 days.

(21) Appl. No.: 12/386,723

(22) Filed: Apr. 22, 2009

Related U.S. Application Data

(60) Provisional application No. 61/125,191, filed on Apr. 23, 2008.

(51) Int. Cl.
*A01H 5/00* (2006.01)

(52) U.S. Cl. ..... Plt./295
(58) Field of Classification Search ..... Plt./295
See application file for complete search history.

(56) References Cited

U.S. PATENT DOCUMENTS

PP15,463 P3 1/2005 Redman
PP18,359 P2 12/2007 Parham

*Primary Examiner*—Annette H Para
(74) *Attorney, Agent, or Firm*—Phase M, LLP

(57) ABSTRACT

A new variety of *Chrysanthemum* plant named 'Letitia Time Sunny', having large yellow single flowers with a lime green disc. 'Letitia Time Sunny' has a wide branching habit with a good foliage presentation.

1 Drawing Sheet

Latin name of the genus and species:
Botanical classification: *Chrysanthemum morifolium.*
Variety denomination: The new *Chrysanthemum* variety denomination is 'Letitia Time Sunny'.

BACKGROUND OF THE INVENTION

The present invention comprises a new and distinct cultivar of *Chrysanthemum* botanically known as *Chrysanthemum morifolium*, and referred to by the cultivar name 'Letitia Time Sunny'.

'Letitia Time Sunny', identified as 22082-1, was discovered as a naturally occurring whole plant mutation in a controlled cultivated planting of the variety 'Letitia Time Improved' (U.S. Plant Pat. No. 18,359).

The new variety 'Letitia Time Sunny' has been asexually reproduced by vegetative cuttings in Chichester, West Sussex, United Kingdom and the distinguishing characteristics are retained through successive generations of asexual reproduction.

BRIEF SUMMARY OF THE INVENTION

'Letitia Time Sunny' is a pot type of *Chrysanthemum* plant variety having large yellow single flowers.

COMPARISON WITH ORIGINAL CULTIVAR

Plants of the new *Chrysanthemum* variety 'Letitia Time Sunny' are similar to the original cultivar 'Letitia Time Improved' in plant habit and growth rate. However, in side-by-side comparisons in Chichester, West Sussex, United Kingdom, under commercial practice, plants of the new *Chrysanthemum* variety 'Letitia Time Sunny' differed from plants of the original cultivar 'Letitia Time Improved' in the following characteristic:

1. The new variety 'Letitia Time Sunny' produces yellow single flowers whereas the original cultivar 'Letitia Time Improved' produces large creamy white single flowers.

COMPARISON WITH SWING TIME YELLOW

Plants of the new *Chrysanthemum* variety 'Letitia Time Sunny' are dissimilar to plants of the variety 'Swing Time Yellow', U.S. Plant Pat. No. 15,463, in plant habit and growth rate. In side-by-side comparisons in Chichester, West Sussex, United Kingdom, under commercial practice, plants of the new *Chrysanthemum* variety 'Letitia Time Sunny' compared to plants of 'Swing Time Yellow' in the following characteristics:

1. The new variety 'Letitia Time Sunny' produces yellow single flowers whereas 'Swing Time Yellow' produces orange yellow single flowers.
2. Plants of the new variety 'Letitia Time Sunny' have larger and taller inflorescence than plants of 'Swing Time Yellow'.
3. The new variety 'Letitia Time Sunny' has a faster response than plants of 'Swing Time Yellow'.

BRIEF DESCRIPTION OF ILLUSTRATIONS

Typical specimens of the plant and flowers for the new *Chrysanthemum* variety 'Letitia Time Sunny' are shown in the accompanying digital photograph. The colors shown are as true as possible within the usual limits of this kind of illustration. FIG. 1 is a whole plant view of the new variety 'Letitia Time Sunny' grown in a pot. The plant shown in the illustration is 56 days from the onset of Short Days.

DETAILED BOTANICAL DESCRIPTION

The following description of the new *Chrysanthemum* variety 'Letitia Time Sunny' is of plants grown in a greenhouse in Chichester, West Sussex, United Kingdom, in the month of April. The cultivar has not been observed under all possible environmental conditions. The phenotype may vary significantly with variations in the environment such as temperature, length of day and light intensity, without any variance in genotype. The commercial classification of the new variety is a Pot *Chrysanthemum.*

Plants of the new variety have been grown successfully under temperature conditions averaging about 18° C. at night and about 24° C. to 25° C. during the day under assimilated light conditions of about 2500 lux. The plants respond well to the use of growth retardant, such as 3-4 applications of B9 with an average dosage of about 2 gram per liter. To produce a commercial product, the plants may be pinched once with the center bud removed. The typical container size for commercial growth is 1 liter. It has been observed that the shelf life of the new variety is about 28 days with a response time of about 7½ weeks. The new variety is suitable for growth in a temperature range of about 15° C. to 25° C.

The following description is with respect to a plant produced as pot *Chrysanthemum*. In the description of this new *Chrysanthemum* variety, color values have been taken from The Royal Horticultural Society Colour Chart (R.H.S.C.C.) by comparison to the new *Chrysanthemum* variety itself and may differ from the colors shown in the accompanying photograph.

Plant

Plant type: Pot.
Habit: Upright and free branching.
Height (cm): 19.
Width (cm): 26.
Stem:
- *Length* (*cm*).—5.
- *Diameter* (*cm*).—0.6.
- *Texture.*—Slightly pubescent.
- *Color.*—138B.

Branching characteristics: Upright and free branching.
Lateral branches:
- *Length* (*cm*): 10.
- *Diameter* (*cm*): 0.4.
- *Texture.*—Slightly pubescent.

Number of breaks from Pinch: 6.
Response Time: 52 days.
Vigor: Medium/Tall.
Shelf Life: 28 days.
Life of blooms: 28 days
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of about 2 gm/liter B9 @ 2, 21 and 28 days after sticking unrooted cuttings.

The plants were grown for two weeks in Long Day conditions (20 hours of light) and then transferred to Short Day conditions (13 hours of dark).

Propagation:
- *Type.*—Vegetative propagation via stem cuttings.
- *Time to rooting.*—14 days with soil temperatures of 18° C.
- *Rooting habit: After* 7 Long Days, the first roots emerge and form root primordia.

In 14 Long Days, a complete root system is developed.

FOLIAGE

Number of leaves per lateral branch: 10.
Compound or single: Single.
Arrangement of leaves: Alternate.
- *Shape of Leaf.*—Typically 5 lobed.
- *Size of Leaf.*—Width (cm): 4 Length (cm): 6.
- *Leaf apex.*—Acute.
- *Base.*—Obtuse.
- *Attachment.*—Petioled.
- *Aspect.*—Slightly undulating.
- *Margin.*—Palmately lobed.
- *Surface characteristics.*—Top: Slightly pubescent. Bottom: Pubescent.

Petiole:
- *Color.*—137B.
- *Length* (*cm*).—2.5.
- *Diameter* (*cm*).—0.4.
- *Surface.*—Slightly pubescent.

Venation: net, prominent lateral and mid-veins at underside.
- *Color.*—Upper side: 138B. Under side: 138B.

Color:
- *Mature Leaf, upper side.*—137A; under side: 138A.
- *Young Leaf, upper side.*—137A; under side: 138A.

FLOWER

Flower appearance: Matte.
Flower type: Single.
Flower form: Slightly cupped.
Flower shape: Circular.
Flowering habit: Cyme.
Number of blossoms per branch: 6.
Typical and observed flowering season: January to December.
Inflorescence form: Cyme.
- *Depth of fully expanded blossoms* (*cm*).—1.8.
- *Diameter of fully expanded blossoms* (*cm*).—8.

Phyllaries:
- *Number.*—36.
- *Color.*—137C.
- *Length* (*cm*).—0.7.
- *Width* (*cm*).—0.2.
- *Texture/appearance.*—Slightly pubescent.

Peduncle:
- *Length* (*cm*).—10.
- *Diameter* (*cm*).—0.4.
- *Angle from stem* (*degrees*).—15.
- *Color.*—138B.
- *Surface.*—Slightly Pubescent.
- *Habit.*—Slightly undulating.
- *Strength.*—Strong.

Pedicel:
- *Length.*—Terminal (cm): 3; lateral (cm): 3.5.
- *Diameter* (*cm*).—0.2.
- *Color.*—138B.
- *Angle from the stem* (*degrees*).—15.
- *Surface.*—Slightly pubescent.
- *Habit.*—Straight.
- *Strength.*—Moderate.

Ray florets:
*Form/shape.*—Straight with parallel edges to the central mid vein.
*Texture/appearance.*—Matte.
*Number per flower.*—24.
*Length* (*cm*).—3.5 Width (cm): 1.
*Apex.*—Rounded.
*Base.*—Tapered.
*Margin.*—Entire.
Disc florets:
*Form/shape.*—Cylindric.
*Texture/appearance.*—Shiny.
*Number per flower.*—200.
*Length* (*cm*).—0.6; Width (cm): 0.1.
*Diameter of disc* (*cm*).—1.5.
Fragrance: None.
Flower bud (at onset of color):
*Length* (*cm*).—1.
*Diameter* (*cm*).—1.2.
*Form/shape.*—Globular.
General flower color:
1. *Ray florets, upper side.*—Immature: 7A. Mature: 7A. Older/fading: 7B
2. *Ray florets, under side.*—Immature: 4A. Mature: 4A. Older/fading: 4A.
3. *Disc florets.*—Immature: 144A. Mature: 144B. Older/fading: 144C.
4. *Bud* (*at onset of color*).—5B.

Flower progression with age: There is no change with the flower form but there is a very slight change of colour with age.

REPRODUCTIVE ORGANS

Gynoecium present on Ray and Disc florets.
Ray florets per individual flower: Pistillate.
*Pistil number.*—24.
*Stigma color.*—154A.
*Stigma shape.*—Forked.
*Style color.*—154B.
*Style length* (*cm*).—0.3.
Disc florets per individual flower: Pistillate.
*Pistil number.*—200.
*Stigma color.*—154A.
*Stigma shape.*—Forked.
*Style color.*—154B.
*Style length* (*cm*).—0.3.
Androecium: Not observed.
Fruit and seeds: None observed.

What is claimed is:

1. A new and distinct variety of *Chrysanthemum* plant, substantially as described and illustrated herein.

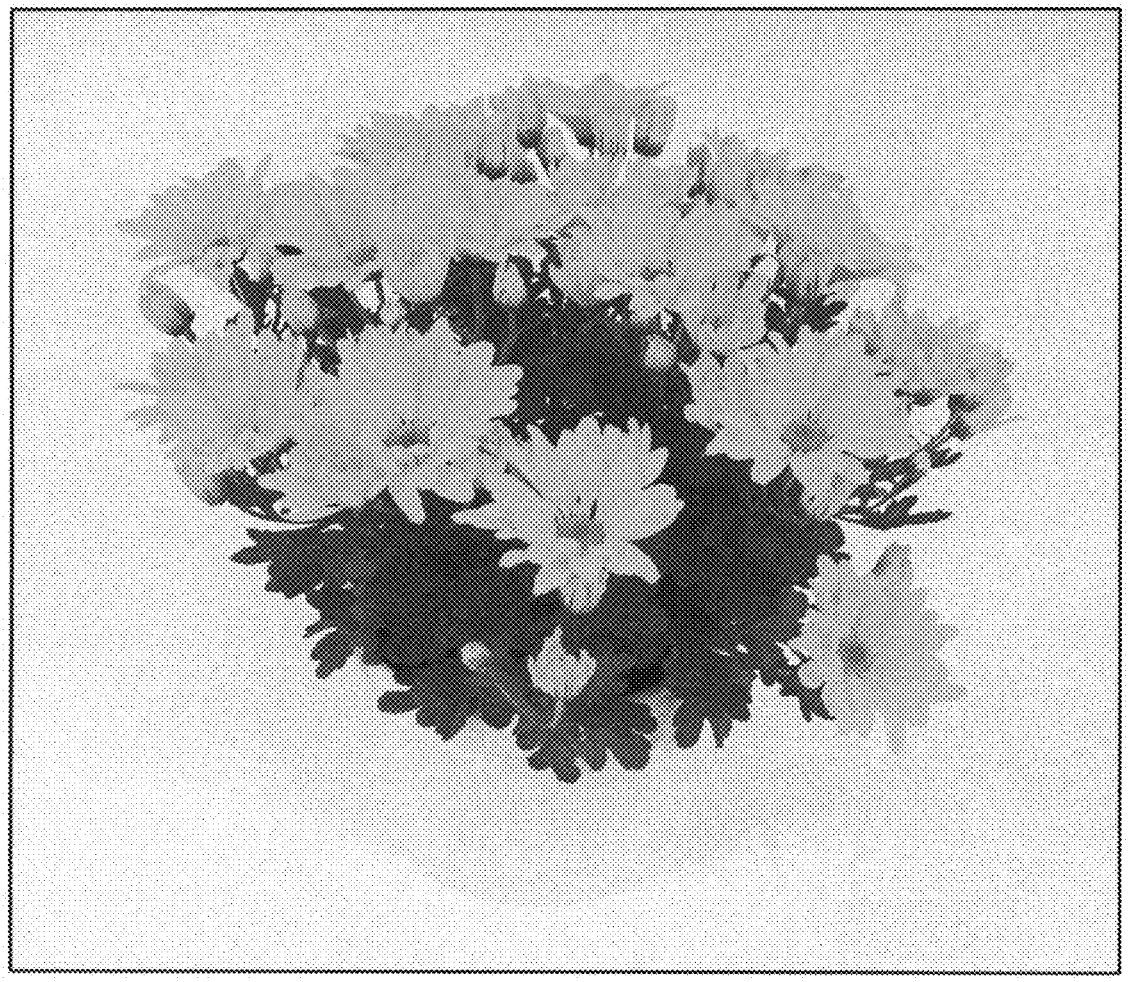

* * * * *